(12) United States Patent
Simon et al.

(10) Patent No.: US 7,244,741 B2
(45) Date of Patent: Jul. 17, 2007

(54) FREDERICAMYCIN DERIVATIVES AS MEDICAMENTS FOR TREATING TUMOURS

(75) Inventors: Werner Simon, Hüffelsheim (DE); Ulrich Abel, Heidelberg (DE)

(73) Assignee: Biofrontera Discovery GmbH (DE)

( * ) Notice: Subject to any disclaimer, the term of this patent is extended or adjusted under 35 U.S.C. 154(b) by 63 days.

(21) Appl. No.: 10/520,421

(22) PCT Filed: Jul. 9, 2003

(86) PCT No.: PCT/EP03/07427

§ 371 (c)(1),
(2), (4) Date: Jan. 6, 2005

(87) PCT Pub. No.: WO2004/004713

PCT Pub. Date: Jan. 15, 2004

(65) Prior Publication Data

US 2005/0215579 A1    Sep. 29, 2005

(30) Foreign Application Priority Data

Jul. 9, 2002    (DE)   ................. 102 30 917

(51) Int. Cl.
*A61K 31/473* (2006.01)
*C07D 221/20* (2006.01)
(52) U.S. Cl. ................. 514/278; 546/15; 546/18
(58) Field of Classification Search ................ 514/278; 546/15, 18
See application file for complete search history.

(56) References Cited

U.S. PATENT DOCUMENTS

| | | | |
|---|---|---|---|
| 4,584,377 A | 4/1986 | Yokoi et al. |
| 4,673,678 A | 6/1987 | Misra |
| 5,166,208 A | 11/1992 | Kelly et al. |

OTHER PUBLICATIONS

Latham, Michael et al.: "Inhibition of Topoisomerases By Fredericamycin A," Cancer Chemotherapy and Pharmacology (1989) 24: 167-171.

Warnick-Pickle, Dana J. et al.: "Fredericamycin A. A New Antitumor Antibiotic Biological Properties," Journal of Antibiotics (1981) vol. 34, No. 11, pp. 1402-1407.

*Primary Examiner*—Charanjit S. Aulakh
(74) *Attorney, Agent, or Firm*—Connolly Bove Lodge & Hutz LLP

(57) ABSTRACT

The invention relates to novel fredericamycin derivatives of general formula (Ia) or (Ib), to medicaments containing the fredericamycin derivatives or salts thereof, and to the use of the fredericamycin derivatives for treating diseases, especially tumor diseases.

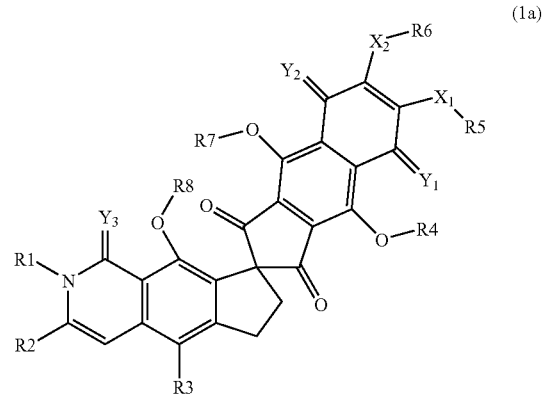

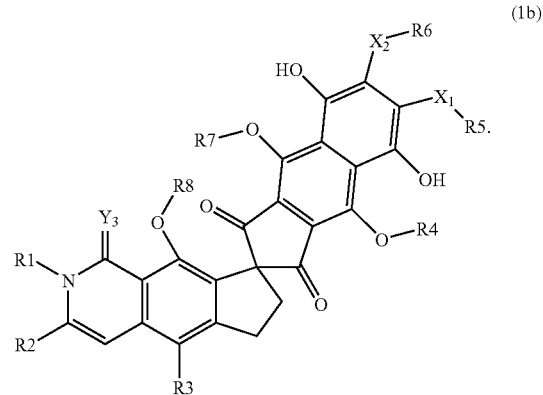

21 Claims, No Drawings

FREDERICAMYCIN DERIVATIVES AS MEDICAMENTS FOR TREATING TUMOURS

RELATED APPLICATIONS

This application is a national stage application (under 35 U.S.C. 371) of PCT/EP03/007427 filed Jul. 9, 2003, which claims benefit to German application number 102 30 917.5 filed Jul. 9, 2002.

The invention relates to novel fredericamycin derivatives, to drugs containing said derivatives or the salts thereof, and to the use of the fredericamycin derivatives for treating diseases, particularly tumor diseases.

Fredericamycin has been isolated 1981 from *Streptomyces griseus*, and demonstrates anti-tumor activity.

Fredericamycin and several fredericamycin derivatives are known.

In Heterocycles 37 (1994) 1893-1912, J. Am. Chem. Soc. 116 (1994) 9921-9926, J. Am. Chem. Soc. 116 (1994) 11275-11286, J. Am. Chem. Soc. 117 (1995) 11839-11849, and in J. Am. Chem. Soc. 123 (2001), various total syntheses of fredericamycin A have been described, some being enantio-selective.

In U.S. Pat. No. 4,673,768, alkali salts of the fredericamycin A are described. In U.S. Pat. No. 4,584,377, fredericamycin derivatives are described, particularly derivatives acylated at ring E and F. In U.S. Pat. No. 5,166,208, fredericamycin derivatives are described as well, particularly derivatives carrying thio and amino substituents in ring F. The derivatives are generated semi-synthetically or fully synthetically.

Surprisingly it was found that fredericamycin derivatives, especially those derivatized in ring E, in ring F, or at rings E and F, represent potent drugs. Also, a possibility was found to introduce such residues in ring E, in ring F, or at both rings E and F semi-synthetically, with which the water solubility, among others, of the derivatives can be significantly increased. Other derivatisation methods known from the art can also be performed with the derivatives according to the invention. Furthermore, an alternative method was found to make fredericamycin derivatives water-soluble by generating cyclodextrin inclusion compounds.

The invention relates to novel fredericamycin derivatives with the general Formula Ia or Ib:

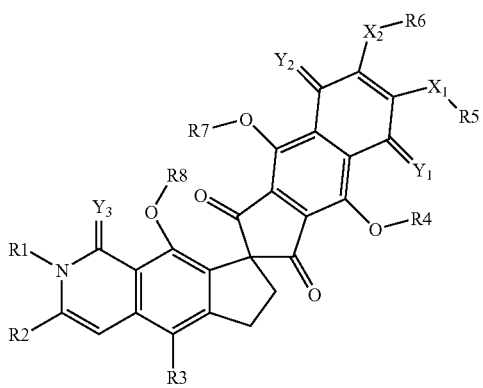

Ia

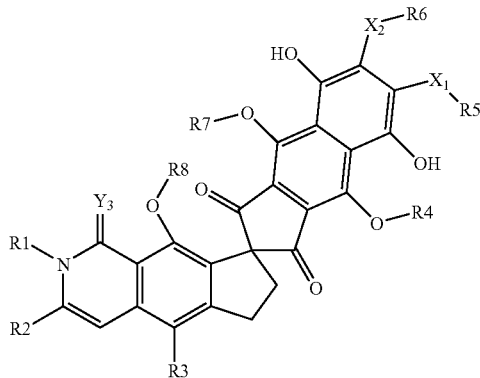

Ib wherein in each,

R1 mean is H, $C_1$-$C_6$ alkyl, cycloalkyl, $C_1$-$C_4$ alkylcycloalkyl,

R2 means $C_1$-$C_{14}$ alkyl, $C_2$-$C_{14}$ alkenyl, $C_1$-$C_4$ alkylaryl, heteroaryl, $C_1$-$C_4$ alkyl heteroaryl, cycloalkyl, $C_1$-$C_4$ alkyl-cycloalkyl, heterocycloalkyl, $C_1$-$C_4$ alkylheterocycloalkyl, $C_mH_{2m+o-p}Y_p$ (with m=1 to 6, for o=1, p=1 to 2m+o; for m=2 to 6, o=-1, p=1 to 2m+o; for m=4 to 6, o=-2, p=1 to 2m+o; Y=independently from each other selected from the group consisting of halogen, OH, OR21, $NH_2$, NHR21, NR21R22, SH, SR21), $CH_2NHCOR21$, $CH_2NHCSR21$, $CH_2S(O)nR21$, with n=0, 1, 2, $CH_2SCOR21$, $CH_2OSO_2$—R21, CHO, CH=NOH, CH(OH)R21, —CH=NOR21, —CH=NOCOR21, —CH=NOCH$_2$CONR21R22, —CH=NOCH(CH$_3$)CONR21R22, —CH=NOC(CH$_3$)$_2$CONR21R22, —CH=N—NHCO—R23, —CH=N—NHCO—CH$_2$NHCOR21, —CH=N—O—CH$_2$NHCOR21, —CH=N—NHCS—R23, —CH=CR24R25 (trans or cis), COOH, COOR21, CONR21R22, —CH=NR21, —CH=N—NR21R22,

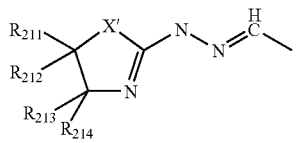

(with X'=NR215, O, S, and R211, R212, R213, R214, R215 being independently from each other H or $C_1$-$C_6$ alkyl), —CH=N—NHSO$_2$ aryl, —CH=N—NHSO$_2$ heteroaryl, R21, R22 are independently from each other $C_1$-$C_{14}$ alkyl, $C_1$-$C_{14}$ alkanoyl, $C_1$-$C_6$ alkylhydroxy, $C_1$-$C_6$ alkylamino, $C_1$-$C_6$ alkylamino-$C_1$-$C_6$ alkyl, $C_1$-$C_6$ alkylamino-di-$C_1$-$C_6$ alkyl, cycloalkyl, $C_1$-$C_4$ alkylcycloalkyl, heterocycloalkyl, $C_1$-$C_4$ alkylheterocycloalkyl, aryl, aryloyl, $C_1$-$C_4$ alkylaryl, heteroaryl, heteroaryloyl, $C_1$-$C_4$ alkylheteroaryl, cycloalkanoyl, $C_1$-$C_4$ alkanoylcycloalkyl, heterocycloalkanoyl, $C_1$-$C_4$ alkanoylheterocycloalkyl, $C_1$-$C_4$ alkanoylaryl, $C_1$-$C_4$ alkanoylheteroaryl, mono- and di-sugar residues linked through a C atom which would carry an OH residue in the sugar, wherein the sugars are independently from each other selected from the group consisting of glucuronic acid and its stereo isomers at all optical C-atoms, aldopentoses, aldohexoses, including their desoxy compounds (such as e.g. glucose, desoxyglucose, ribose, desoxyribose), R23 independently of R21, has the same meanings as R21, or CH$_2$-pyridinium salts, CH$_2$-tri-C$_1$-C$_6$ alkylammonium salts, R24 independently of R21, has the same meanings as R21, or H, CN, COCH$_3$, COOH, COOR21, CONR21R22, NH$_2$, NHCOR21, R25 independently of R21, has the same meanings as R21, or H, CN, COCH$_3$, COOH, COOR21, CONR21R22, NH$_2$, NHCOR21, R24, R25 together mean C$_4$-C$_8$ cycloalkyl, R3 means H, F, Cl, Br, I, OH, OR31, NO$_2$, NH$_2$, NHR31, NR31R32, NHCHO, NHCOR31, NHCOCF3, CH$_{3-m}$hal$_m$ (with hal=Cl, F, especially F, and m=1, 2, 3), OCOR31, R31, 32 independently from each other mean C$_1$-C$_6$ alkyl, R5, R6 independently from each other mean H, C$_1$-C$_{14}$ alkyl, C$_2$-C$_{14}$ alkenyl, aryl, C$_1$-C$_4$ alkylaryl, heteroaryl, C$_1$-C$_4$ alkylheteroaryl, cycloalkyl, C$_1$-C$_4$ alkylcycloalkyl, heterocycloalkyl, C$_1$-C$_4$ alkylheterocycloalkyl, C$_m$H$_{2m+o-p}$Y$_p$ (with m=1 to 6, for o=1, p=1 to 2m+o; for m=2 to 6, o=-1, p=1 to 2m+o; for m=4 to 6, o=-2, p=1 to 2m=o; Y=independently selected from the group consisting of halogen, OH, OR21, NH$_2$, NHR21, NR21R22, SH, SR21), or R5 and R6, together with X$_1$—C—C—X$_2$, form a ring with 5, 6, or 7 members, R4, R7, R8 independently from each other mean H, C$_1$-C$_6$ alkyl, CO—R41, R41 independently from R21 has the same meanings as R21, X1 means O, S, NH, N—C$_1$-C$_8$ alkyl, N-cycloalkyl, X2 means O, S, NH, N—C$_1$-C$_8$ alkyl, N-cycloalkyl, Y1 means O, N—R9, wherein R9 can, independently from R5, adopt the same meanings as R5, Y2 means O, N—R10, wherein R10 can, independently from R5, adopt the same meanings as R5, and, if Y1 or Y2 are N—R9 or N—R10, X2-R6 may be H, Y3 means O, S, NH, as well their stereoisomers, tautomers, and their physiologically tolerable salts or inclusion compounds.

Preferred are compounds of Formula IIa or IIb

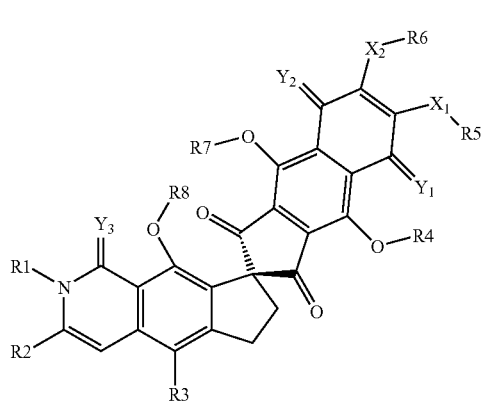

IIa

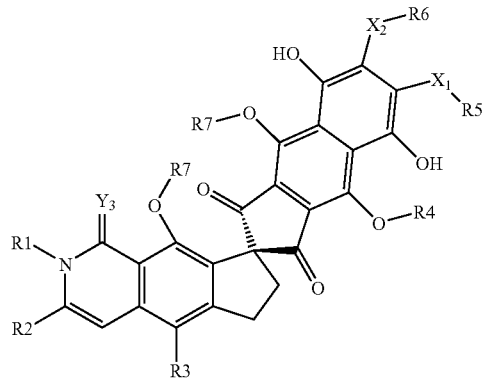

IIb wherein the meaning of the residues R1-R41, X1, X2, Y1 and Y2 is as described above, their tautomers and their physiologically tolerable salts or inclusion compounds.

The invention also relates to compounds of the Formula Ia, Ib, IIa or IIb, in which the residues R have the above described meanings, and the water solubility of R2 is at least two times higher, preferably at least five timer higher, more preferred at least ten times higher, especially preferred at least fifty time higher, particularly one hundred times higher, or even five hundred times higher than of R2 being CH=CH—CH=CH—CH$_3$, when all other residues are maintained. The increase in water solubility is mediated e.g. by introduction of groups which can increasingly form hydrogen bonds and/or are polar and/or ionic. A key intermediate product are compounds with an aldehyde function in R2. Preferred are aldehydes and the thereof derived compounds, in which at least R1 or R3 not equal H, when R4 to R8 are H or alkyl.

Preferred R2 residues are heteroaryl, cycloalkyl, C$_1$-C$_4$ alkylcycloalkyl, heterocycloalkyl, C$_1$-C$_4$ alkylheterocycloalkyl, C$_m$H$_{2m+o-p}$Y$_p$ (with m=1 to 6, for o=1, p=1 to 2-o; for m=2 to 6, o=-1, p=1 to 2m+o; for m=4 to 6, o=-2, p=1 to 2m+o; Y=independently selected from each other from the group of halogen, OH, OR21, NH$_2$, NHR21, NR21R22, SH, SR21), CH$_2$NHCOR21, CH$_2$NHCSR21, CH$_2$S(O)nR21, with n=0, 1, 2, CH$_2$SCOR21, CH$_2$OSO$_2$—R21, CH(OH)R21, —CH=NOCOR21, —CH=NOCH$_2$CONR21R22, —CH=NOCH(CH$_3$)CONR21R22, —CH=NOC(CH$_3$)$_2$CONR21R22, —CH=N—NHCO—R23, —CH=N—NHCO—CH$_2$NHCOR21, —CH=N—O—CH$_2$NHCOR21, —CH=N—NHCS—R23, —CH=CR24R25 (trans or cis), CONR21R22, —CH=NR21, —CH=N—NR21R22,

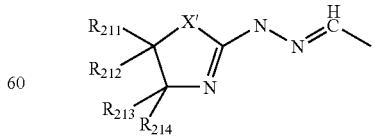

(with X'=NR215, O, S, and R211, R212, R213, R214, R215 being independently from each other H or C$_1$-C$_6$ alkyl), —CH=N—NHSO$_2$ aryl, —CH=N—NHSO$_2$ heteroaryl.

Furthermore preferred are still compounds as described above, wherein the residues R preferably independently from each other adopt one or more of the following meanings:

R1 means H, $C_1$-$C_5$ alkyl, cycloalkyl, especially H,

R2 means $C_1$-$C_5$ alkyl, $C_1$-$C_4$ alkylaryl, $C_2$-$C_5$ alkenyl, heteroaryl, $C_1$-$C_4$ alkylheteroraryl, $CHF_2$, $CF_3$, polyol side chain, particularly CHOH—CHOH—CHOH—CHOH—$CH_3$, CHOH—CHOH—CH=CH—$CH_3$, CH=CH—CHOH—CHOH—$CH_3$, $CH_2$Y (Y=F, Cl, Br, I), $CH_2NH_2$, $CH_2$NR21R22, $CH_2$NHCOR23, $CH_2$NHCSR23, $CH_2$SH, $CH_2$S(O)nR21, with n=0, 1, 2, $CH_2$SCOR21, particularly $CH_2$OH, $CH_2$OR21, $CH_2$OSO$_2$—R21, particularly CHO, CH(OR21)$_2$, CH(SR21)$_2$, CN, CH=NOH, CH=NOR21, CH=NOCOR21, CH=N—NHCO—R23, CH=CR24, R25 (trans or cis), particularly COOH (particularly their physiologically tolerable salts), COOR21, CONR21R22, —CH=NR21, —CH=N—NR21R22,

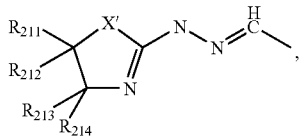

(with X'=NR215, O, S, and R211, R212, R213, R214, R215 being independently from each other H or $C_1$-$C_6$ alkyl), —CH=N—NHSO$_2$ aryl, —CH=N—NHSO$_2$ heteroaryl, CH=N—NHCO—R23, R21, R22 independently from each other mean $C_1$-$C_6$ alkyl, cycloalkyl, aryl, $C_1$-$C_4$ alkylaryl, heteroaryl, $C_1$-$C_4$ alkylheteroaryl, R23 independently of R21, has the same meanings as R21, or $CH_2$-pyridinium salts, $CH_2$-tri-$C_1$-$C_6$ alkylammonium salts, R24 independently of R21, has the same meanings as R21, or H, CN, $COCH_3$, COOH, COOR21, CONR21R22, $NH_2$, NHCOR21, R25 independently of R21, has the same meanings as R21, or H, CN, $COCH_3$, COOH, COOR21, CONR21R22, $NH_2$, NHCOR21, R24, R25 together mean $C_4$-$C_8$ cycloalkyl, R3 means F, Cl, Br, I, NO2, NH2, NHCOR31, R31 independently from each other mean $C_1$-$C_6$ alkyl, R5, R6 independently from each other mean H, $C_1$-$C_{14}$ alkyl, $C_2$-$C_{14}$ alkenyl, aryl, $C_1$-$C_4$ alkylaryl, heteroaryl, $C_1$-$C_4$ alkylheteroaryl, cycloalkyl, $C_1$-$C_4$ alkylcycloalkyl, heterocycloalkyl, $C_1$-$C_4$ alkylheterocycloalkyl, $C_m H_{2m+o-p}Y_p$ (with m=1 to 6, for o=1, p=1 to 2m+o; for m=2 to 6, o=−1, p=1 to 2m+o; for m=4 to 6, o=−2, p=1 to 2m+o; Y=independently selected from the group consisting of halogen, OH, OR21, $NH_2$, NHR21, NR21R22, SH, SR21), or R5 and R6, together with $X_1$—C—C—$X_2$, form a ring with 5, 6, or 7 members, R4, R7, R8 independently from each other mean H, $C_1$-$C_6$ alkyl, CO—R41, R41 independently from R21 has the same meanings as R21, Y3 means O, S, preferably O, as well their stereoisomers, tautomers, and their physiologically tolerable salts or inclusion compounds.

Especially preferred are the compounds, their stereo isomers, tautomers, and physiologically tolerable salts or inclusion compounds selected from the group consisting of the compounds of the examples and the compounds demonstrating combinations of the various substituents of the compounds of these examples.

Also preferred are drugs which contain the above compounds of Formula I or II in addition to the usual carriers and adjuvants.

Also preferred are the above mentioned drugs in combination with other agents for tumor treatment.

These compounds according to the invention are used for preparation of drugs for treatment of tumors, particularly such that may be treated by inhibition of the topoisomerases I and/or II. Tumors that can be treated with the substances according to the invention are e.g. leukemia, lung cancer, melanomas, prostate tumors and colon tumors.

Furthermore, the compounds according to the invention are used for preparation of drugs for treatment of neurodermitis, parasites and for immunosuppression.

In the description and the claims the substituents are described by the following definitions:

The term "alkyl" by itself or as part of another substituent means a linear or branched alkyl chain radical of the respectively indicated length, in which optionally a $CH_2$ group may be substituted by a carbonyl function. Thus, $C_{1-4}$ alkyl may be methyl, ethyl, 1-propyl, 2-propyl, 2-methyl-2-propyl, 2-methyl-1-propyl, 1-butyl, 2-butyl, $C_{1-6}$ alkyl, e.g. $C_{1-4}$ alkyl, pentyl, 1-pentyl, 2-pentyl, 3-pentyl, 1-hexyl, 2-hexyl, 3-hexyl, 4-methyl-1-pentyl, or 3,3-dimethylbutyl.

The term "$C_1$-$C_6$ alkylhydroxy" by itself or as part of another substituent means a linear or branched alkyl chain radical of the respectively indicated length, which may be saturated or unsaturated, and which carries an OH group, e.g. hydroxymethyl, hydroxymethyl, 1-hydroxypropyl, 2-hydroxypropyl.

The term "alkenyl" by itself or as part of another substituent means a linear or branched alkyl chain radical with one or more C=C double bonds of the respectively indicated length, several double bonds being preferably conjugated. Thus, $C_{2-6}$ alkenyl may for example be ethenyl, 1-propenyl, 2-propenyl, 2-methyl-2-propenyl, 2-methyl-1-propenyl, 1-butenyl, 2-butenyl, 1,3-butdienyl, 2,4-butdienyl, 1-pentenyl, 2-pentenyl, 3-pentenyl, 1,3-pentdienyl, 2,4-pentdienyl, 1,4-pentdienyl, 1-hexenyl, 2-hexenyl, 1,3-hediexyl, 4-methyl-1-pentenyl, or 3,3-dimethylbutenyl.

The term "halogen" stands for fluorine, chlorine, bromine, iodine, preferably bromine and chlorine.

The term "NR21R22" stands for a dialkylamino group, wherein the two alkyl groups, together with the N, may also form a ring with 5 or 6 members.

If R5 and R6, together with $X_1$—C—C—$X_2$, form a ring with 5, 6 or 7 members, then R5 and R6 together are preferably $CH_2$, $CH_2$—$CH_2$, CH=CH, $CH_2$—$CH_2$—$CH_2$, CH=CH—$CH_2$, or $CH_2$—CH=CH.

The term "cycloalkyl" by itself or as part of another substituent comprises saturated, cyclic carbohydrate groups with 3 to 8 C atoms, such as e.g. cyclopropyl, cyclobutyl, cyclopentyl, cyclohexyl, 4-methylcyclohexyl, cyclohexylmethylene, cycloheptyl or cyclooctyl.

The term "heterocycloalkyl" by itself or as part of another substituent includes cycloalkyl groups, wherein up to two $CH_2$ groups may be substituted by oxygen, sulfur or nitrogen atoms, and another $CH_2$ group may be substituted by a carbonyl function, for example pyrrolidine, piperidine, morpholine or

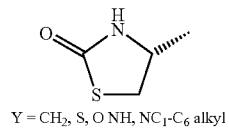 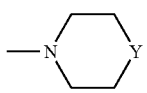 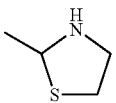

Y = CH₂, S, O NH, NC₁-C₆ alkyl

The term "aryl" by itself or as part of another substituent includes aromatic ring systems with up to 3 rings, in which at least 1 ring system is aromatic, and those with up to 3 substituents, preferably up to 1 substituent, wherein the substituents independently from each other can have the meaning $C_1$-$C_6$ alkyl, OH, $NO_2$, CN, $CF_3$, OR11, SH, SR11, $C_1$-$C_6$ alkylhydroxy, $C_1$-$C_6$ alkyl-OR11, COOH, COOR11, NH2, NHR11, NR11R12, halogen, wherein the residues R11, R12 independently from each other can mean $C_1$-$C_{10}$ alkyl, cycloalkyl, $C_1$-$C_4$ alkylcycloalkyl.

Apart from phenyl and 1-naphthyl and 2-naphthyl, preferred aryls are:

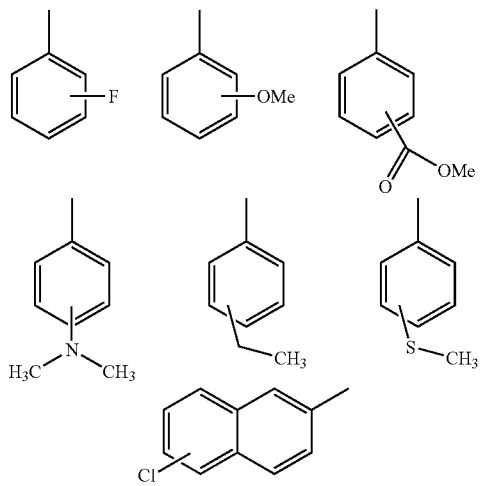

The term "heteroaryl" by itself or as part of another substituent includes aromatic ring systems with up to 3 rings and with up to 3 identical or different heteroatoms N, S, O, in which at least 1 ring system is aromatic, and those with up to 3 substituents, preferably up to 1 substituent, wherein the substituents independently from each other can have the meaning $C_1$-$C_6$ alkyl, OH, $NO_2$, CN, $CF_3$, OR11, SH, SR11, $C_1$-$C_6$ alkylhydroxy, $C_1$-$C_6$ alkyl-OR11, COOH, COOR11, $NH_2$, NHR11, NR11R12, halogen, wherein the residues R11 independently from each other can have the above indicated meanings.

Preferred heteroaryls are:

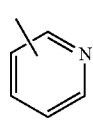 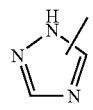 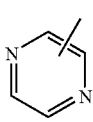

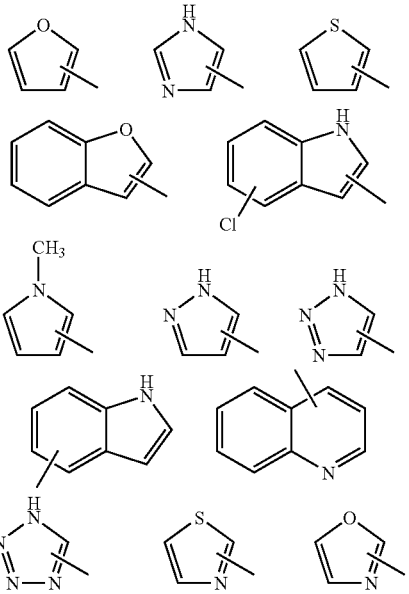

The term "ring system" generally refers to rings with 3, 4, 5, 6, 7, 8, 9, or 10 members. Preferred are rings with 5 and 6 members. Furthermore, ring systems with one or 2 annelated rings are preferred.

The compounds of Formula I may be present as such, or, if they contain acidic or basic groups, in the form of their salts with physiologically tolerable bases or acids. Examples for such acids are: hydrochloric acid, citric acid, trifluoracetic acid, tartaric acid, lactic acid, phosphoric acid, methane sulfonic acid, acetic acid, formic acid, maleic acid, fumaric acid, succinic acid, hydroxysuccinic acid, sulfuric acid, glutaric acid, aspartic acid, pyruvic acid, benzoic acid, glucuronic acid, oxalic acid, ascorbic acid, and acetylglycine. Examples for bases are alkali ions, preferably Na, K, alkaline earth ions, preferably C, Mg, ammonium ions.

The compounds according to the invention may be administered orally in the usual way. The application may also be i.v., i.m., with vapors, or sprays through the nasopharynx.

The dosage depends on age, condition and weight of the patient as well as on the type of application. Usually, the daily dose of the active ingredient per person is between 0.1 μg/kg and 1 g/kg orally. This dosage may be given as 2 to 4 split dosages, or once per day as a slow release form.

The novel compounds may be used in the usual solid or liquid pharmaceutical application forms, e.g. as tablets, film tablets, capsules, powder, granules, coated tablets, solutions, or sprays. These are prepared in the usual way. The agents can be processed with the usual pharmaceutical adjuvants such as tablet binders, fillers, preservatives, disintegrants, flow regulators, plasticizers, wetting agents, dispersants, emulsifiers, solvents, retardation agents, antioxidants, and/or propellants (see H. Sucker et al.: Pharmazeutische Technologie, Thieme-Verlag, Stuttgart, 1978). Usually, the so obtained application forms contain the active ingredient in amounts of 0.1 to 99 percent per weight.

Experimental Part

Fredericamycin A can be prepared by fermentation or fully synthetically according to the known methods. The reduced forms of the Formulas Ib and IIb can be obtained from the appropriate compounds of Formulas Ia and IIa using mild reducing agents.

Preparation of the Substances

For the synthesis of water soluble fredericamycin derivatives, fredericamycin (1) was first hydroxylated with osmium(IV)oxide at the diene side chain (see diagram 1).

Diagram 1

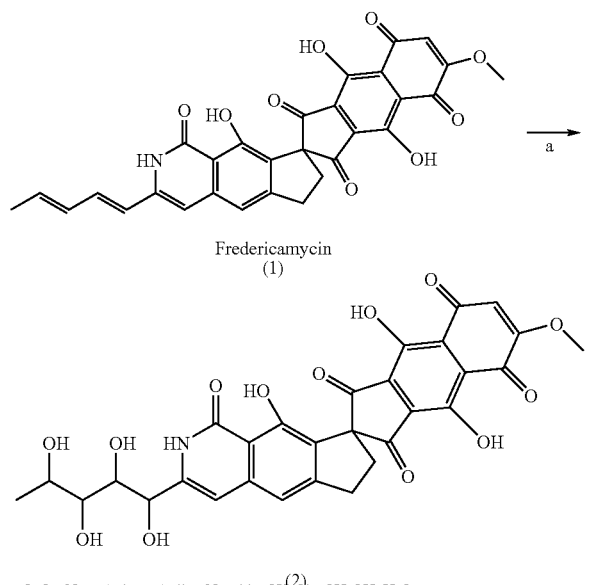

a OsO₄, N-methylmorpholine-N-oxide, CH₂Cl₂, CH₃OH, H₂O

The fredericamyin tetrol (10) also serves as an important intermediate for the synthesis of the herein mentioned fredericamyin derivatives with increased solubility and/or efficacy profile. By iodine cleavage with sodium metaperiodate or carrier-bound periodate, the tetrol side chain can be broken down to the fredericamycin aldehyde (4) with very high yields (see diagram 2).

Diagram 2

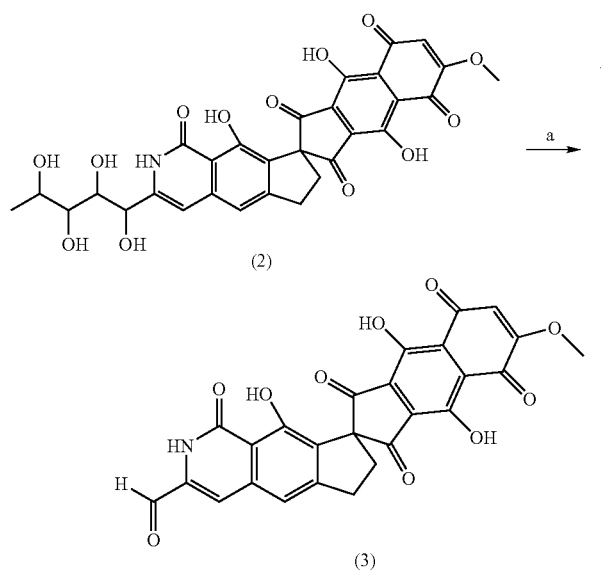

a NaIO₄—H₂O—DMF or carrier-bound —IO₄—H₂O—DMF

The fredericamycin aldehyde (3) can be reacted with acylhydrazones, hydroxylamine and O-alkylhydroxylamine to the corresponding hydrazone (see diagram 3) or oxime and oxime ether (see diagram 4). The reaction can be performed at room temperature in solvents such as DMF or pyridine, and is finished after several minutes to hours.

Diagram 3

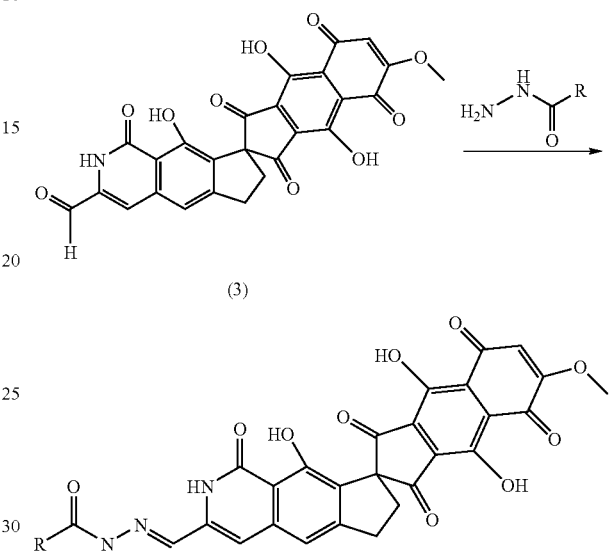

Diagram 4

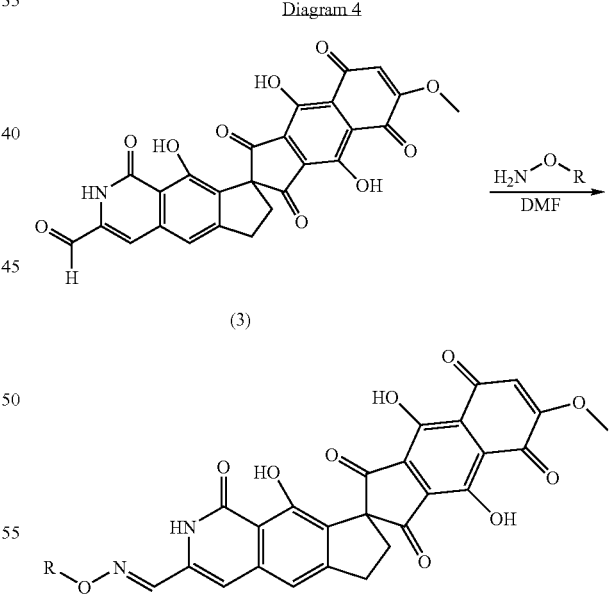

Halogen-substituted Fredericamycin Derivatives R=I, Br, Cl, F

Fredericamycin (1) can be reacted with halogenization agents such as N-bromosuccinimide (NBS) and N-iodosuccinimide (NIS) to the substituted 5-bromo- or 5 iodofredericamyin derivatives (4) and (5) with good yields (diagram 5).

The corresponding fluorine compound is also accessible.

Diagram 5
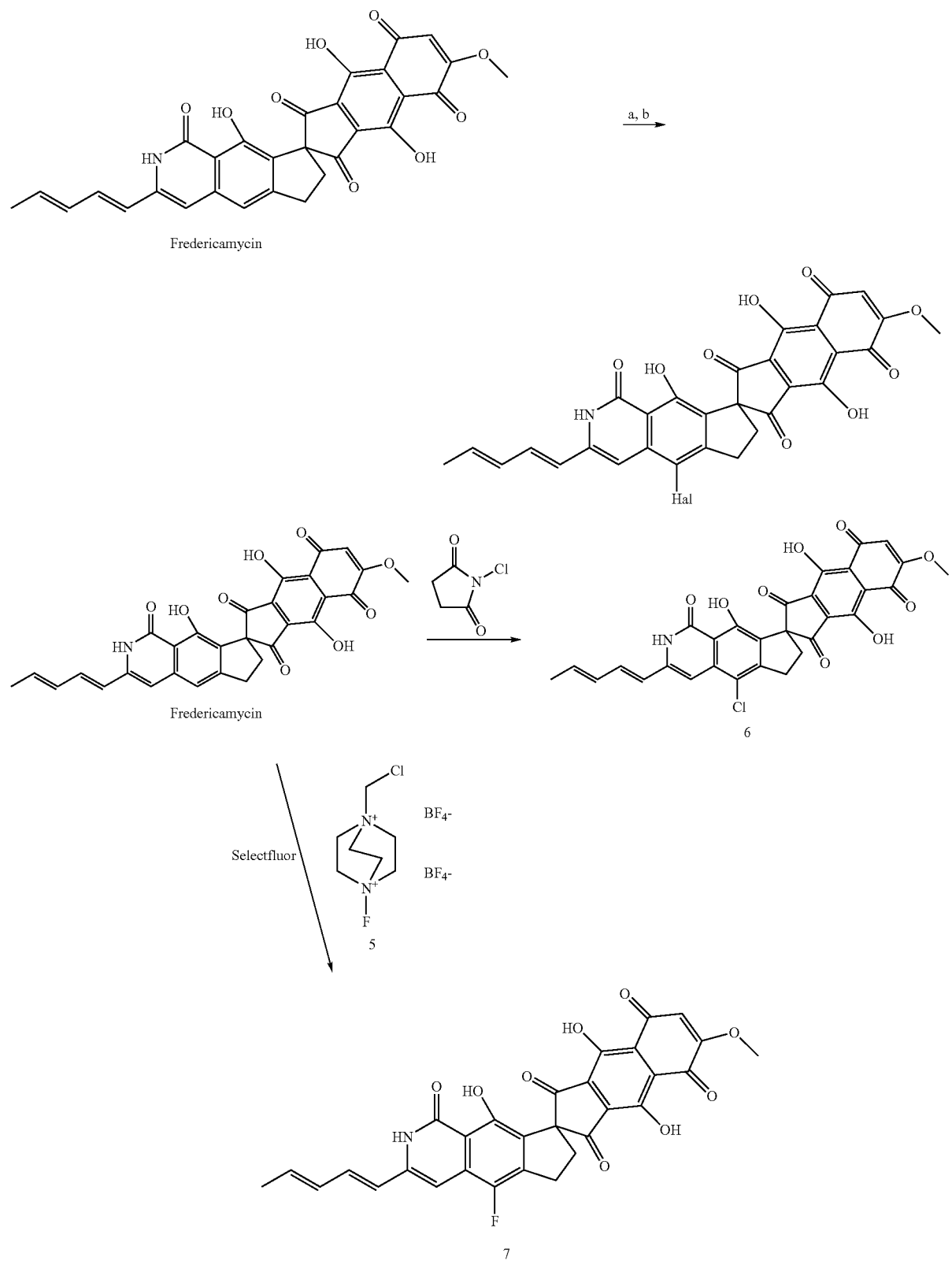

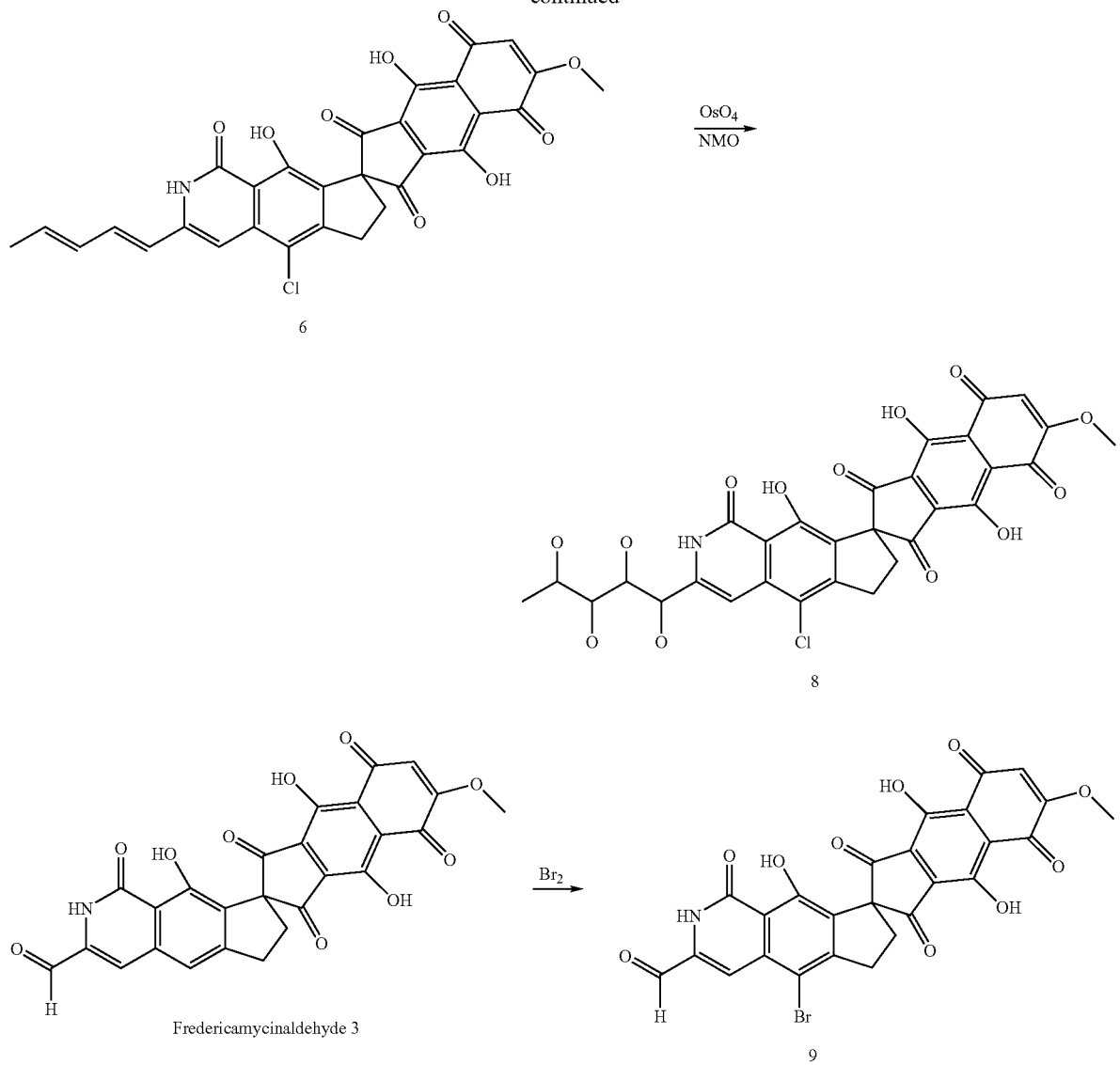
a N-bromosuccinimide, DMF, 0° C.;
b N-iodosuccinimide, DMF, 0° C.;
Hal: Br (4), I (5)
The here named fredericamycin derivatives may then be converted into the claimed compounds by reactions with the corresponding S or N nuclophiles. Diagram 6.
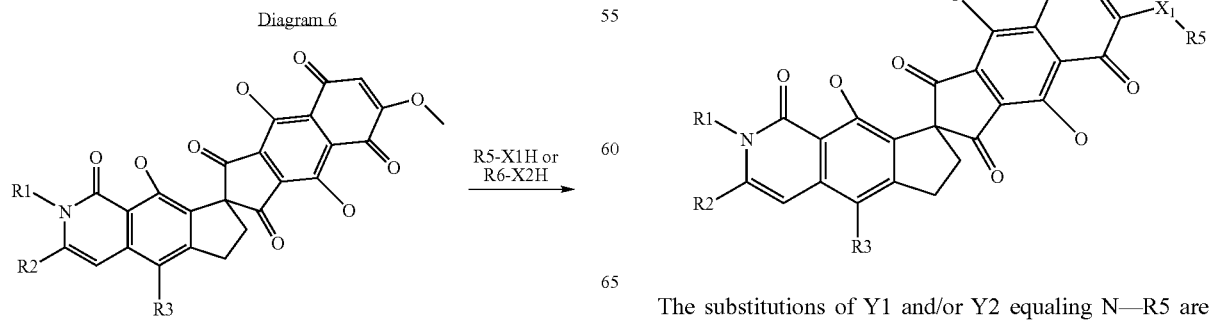
The substitutions of Y1 and/or Y2 equaling N—R5 are accessible over corresponding primary amines HN—R5.

SYNTHESIS EXAMPLES

TABLE 1

| R3 | X1—R5 | X2—R6 | Example |
|---|---|---|---|
| H | OMe | SCH2COOEt | 1 |
| H | OH | SCH2CH2NEt2 | 2 |
| H | OMe | SCH2CH2OH | 3 |
| H | OMe | SCH2CH2Net2 | 4 |
| Cl | OMe | SCH2Ph | 5 |
| H | OMe | OH | 6 |

Preparation of Thioanalogoues of Fredericamycin Derivatives

By sulfuration of fredericamycin or its derivatives with Lawesson reagent or $P_4S_{10}$ in pyridine, the derivatives analogous to thiopyridone are accessible (see diagram 7, therein demonstrated with fredericamycin A).

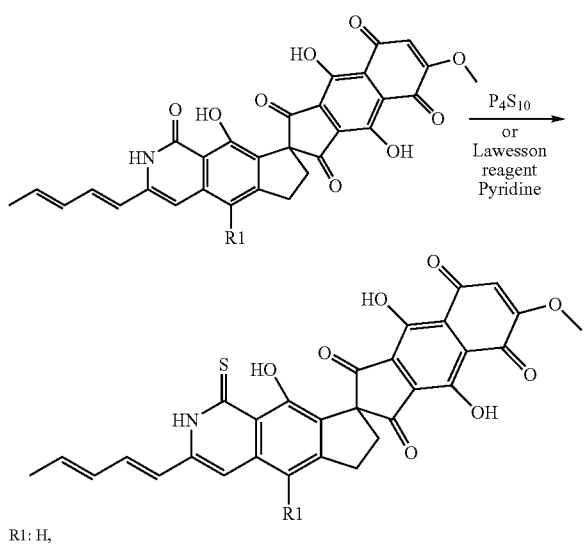

R1: H,

Biological Activity Against 12 Cancer Cell Lines:

LCL (H460/lung), MACL (MCF7, breast), LXFL (529L, lung), LXFA (629L, lung), MEXF (462NL, melanoma), MEXF (514L, melanoma), MAXF (401NL, breast), RXF (944L, renal), RXF (486L, renal), UXF (1138L, uterus), PRXF (PC3M, prostate), PRXF (22RV1).

Efficacy (IC70), averaged over all cell lines in μg/ml with 5 test concentrations.

TABLE 7

| Example/Reference | IC70 μg/ml |
|---|---|
| Adriamycin | 0.0210 |
| Cisplatin | 37.1020 |
| Fredericamycin | 0.2790 |
| 3 | 0.1340 |

EXAMPLES

Example 1

(8S)-4',9,9'-trihydroxy-6'-methoxy-7-ethylthioaceto-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone Ten (10) mg (18.6 μmol) fredericamycin are dissolved under argon in 1 mL DMF, and then 2.5 μl (22.3 μmol) mercaptoacetic acid ethyl ester is added at room temperature. After 24 h, a uniform new product has formed according to HPLC (RP18, acetonitril/water). The reaction mixture is concentrated in the high vacuum until dry.

Red crystal mass. Yield: 12 mg (98%). M/e=558.9 (M+H), $\lambda_{max}$: 510 nm.

Example 2

(8S)-4',9,9'-trihydroxy-6'-methoxy-7(2-methylaminoethylmercapto)-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone Ten (10) mg (18.6 μmol) fredericamycin are dissolved under argon in 1 mL DMF, and then 3.8 mg (22.3 μmol) 2-diethylaminoethanthiol.HCl is added at room temperature. After 23 h, another 3.17 mg 2-diethylaminoethanthiol.HCl is added. After a total reaction time of 45 h, the reaction mixture is concentrated in the high vacuum until dry, and the residue is chromatographed using preparative HPLC (RP18, acetonitril/water).

Red crystal mass. Yield: 4 mg (33%). M/e=657.5 (M+H), $\lambda_{max}$: 486 nm.

Example 3

(8S)-4',9,9'-trihydroxy-6'-methoxy-7(2-hydroxyethylmercapto)-3-[(1E,3E)-penta-1,3-dienyl]-6,7-dihydrospiro[cyclopenta[g]isoquinoline-8,2'-cyclopenta[b]-napthalene]-1,1'-3',5',8'(2H)-pentone Ten (10) mg (18.6 μmol) fredericamycin are dissolved under argon in 1 mL DMF, and then 1.6 μl (22.3 μmol) mercaptoethanol is added at room temperature. After 20 h, a uniform new product has formed according to HPLC (RP18, acetonitril/water). The reaction mixture is concentrated in the high vacuum until dry.

Red crystal mass. Yield: 11 mg (99%). M/e=617.4 (M+H), $\lambda_{max}$: 486 nm.

Example 4

(8S)-4',9,9'-trihydroxy-6'-methoxy-7-(2-diethylaminoethylmercapto)-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone Ten (10) mg (18.6 μmol) fredericamycin are dissolved under argon in 1 mL DMF, and then 3.8 mg (22.3 μmol) 2-diethylaminoethanthiol.HCl is added at room temperature. After 6 h, another 1.9 mg 2-diethylaminoethanthiol.HCl is added. After 23 h, another 1.9 mg 2-diethylaminoethanthiol.HCl is added. After a total reaction time of 30 h, the reaction mixture is concentrated in the high vacuum until dry, and the residue is chromatographed using preparative HPLC (RP18, acetonitril/water).

Red crystal mass. Yield: 10 mg (80%). M/e=671.4 (M+H), $\lambda_{max}$: 486 nm.

Example 5

(8S)-4',9,9'-trihydroxy-6'-methoxy-7-(benzymercapto)-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone Five (5.0) mg (8.71 μmol) 5-chlorofredericamycin are dissolved under argon in 1 mL DMF, and then 1.23 μl (10.45 μmol) benzylmercapto is added at room temperature. After 6 h, another 1.9 mg 2-diethylaminoethanthiol.HCl is added. After 4 h, the reaction mixture is concentrated in the high vacuum until dry.

Red crystal mass. Yield: 6 mg (99%). M/e=695.9 (M+H), $\lambda_{max}$: 504 nm.

Example 6

(8S)-4',9,9'-trihydroxy-6'-methoxy-7-hydroxy-3-[(1E,3E)-penta-1,3-dienyl]-6,7-dihydrospiro[cyclopenta[g]isoquinoline-8,2'-cyclopenta[b]-naphthalene]-1,1'-3',5',8'(2H)-pentone Ten (10) mg (18.6 μmol) fredericamycin are dissolved under argon in 1 mL DMF, and then 2.5 mg (22.3 μmol) 2-aminoethanthiol.HCl is added at room temperature. After 26 h, another 2.1 mg 2-aminoethanthiol.HCl and some trifluoracetic acid is added. After a total reaction time of 72 h, the reaction mixture is concentrated in the high vacuum until dry, and the residue is chromatographed using preparative HPLC (RP18, acetonitril/water).

Red crystal mass. Yield: 9 mg (87%). M/e=554.5 (M–H), $\lambda_{max}$: 372 nm.

What is claimed is:

1. A compound according to the general formula Ia or Ib:

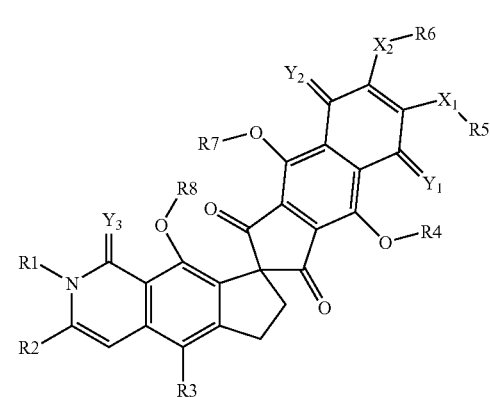

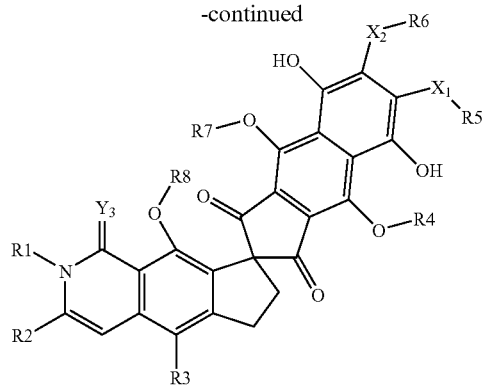

wherein in each,

R1 is H, $C_1$-$C_6$ alkyl, cycloalkyl, or $C_1$-$C_4$ alkylcycloalkyl;

R2 is $C_1$-$C_{14}$ alkyl, $C_2$-$C_{14}$ alkenyl, $C_1$-$C_4$ alkylaryl, heteroaryl, $C_1$-$C_4$ alkyl heteroaryl, cycloalkyl, $C_1$-$C_4$ alkyl-cycloalkyl, heterocycloalkyl, $C_1$-$C_4$ alkylheterocycloalkyl, $C_mH_{2m+o-p}Y_p$, $CH_2NHCOR21$, $CH_2NHCSR21$, $CH_2S(O)nR21$, with n=0, 1, 2, $CH_2SCOR21$, $CH_2OSO_2$—R21, CHO, CH=NOH, CH(OH)R21, —CH=NOR21, —CH=NOCOR21, —CH=NOCH$_2$CONR21R22, —CH=NOCH(CH$_3$)CONR21R22, —CH=NOC(CH$_3$)$_2$CONR21 R22, —CH=N—NHCO—R23, —CH=N—NHCO—CH$_2$NHCOR21, —CH=N—O—CH$_2$NHCOR$_{21}$, —CH=N—NHCS—R23, —CH=CR24R25 (trans or cis), COOH, COOR21, CONR21R22, —CH=NR21, —CH=N—NR21R22,

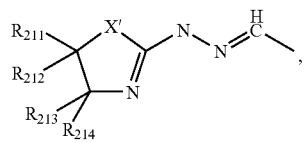

—CH=N—NHSO$_2$ aryl, or —CH=N—NHSO$_2$ heteroaryl;

wherein, m is 1 to 6, o is 1, p is 1 to 2m+o;

m is 2 to 6, o is −1, p is 1 to 2m+o; or m is 4 to 6, o is −2, p is 1 to 2m+o; and Y independently from each other is selected from the group consisting of halogen, OH, OR21, NH$_2$, NHR21, NR21R22, SH and SR21; and wherein X' is NR215, O, or S; and R211, R212, R213, R214, and R215 are independently from each other H or $C_1$-$C_6$ alkyl;

R21, R22 are independently from each other $C_1$-$C_{14}$ alkyl, $C_1$-$C_{14}$ alkanoyl, $C_1$-$C_6$ alkylhydroxy, $C_1$-$C_6$ alkylamino, $C_1$-$C_6$ alkylamino-$C_1$-$C_6$ alkyl, $C_1$-$C_6$ alkylamino-di-$C_1$-$C_6$ alkyl, cycloalkyl, $C_1$-$C_4$ alkylcycloalkyl, heterocycloalkyl, $C_1$-$C_4$ alkylheterocycloalkyl, aryl, aryloyl, $C_1$-$C_4$ alkylaryl, heteroaryl, heteroaryloyl, $C_1$-$C_4$ alkylheteroaryl, cycloalkanoyl, $C_1$-$C_4$ alkanoylcycloalkyl, heterocycloalkanoyl, $C_1$-$C_4$ alkanoylheterocycloalkyl, $C_1$-$C_4$ alkanoylaryl, $C_1$-$C_4$ alkanoylheteroaryl, or mono- and di-sugar linked through a C atom which would carry an OH group in the sugar, wherein the sugars are independently from each other selected from the group consisting of glucuronic acid and its stereo isomers at all optical C-atoms, aldopentoses, and aldohexoses, including their desoxy compounds;

R23 independently of R21, is R21, $CH_2$-pyridinium salts, or $CH_2$-tri-$C_1$-$C_6$ alkylammonium salts;

R24 independently of R21, is R21, H, CN, $COCH_3$, COOH, COOR21, CONR21R22, NH2, or NHCOR21;

R25 independently of R21, is R21, H, CN, $COCH_3$, COOH, COOR21, CONR21R22, $NH_2$, or NHCOR21; or R24, R25 together are $C_4$-$C_8$ cycloalkyl;

R3 is H, F, Cl, Br, I, OH, OR31, $NO_2$, $NH_2$, NHR31, NR31R32, NHCHO, NHCOR31, NHCOCF3, $CH_{3-m}hal_m$ or OCOR31, wherein hal is Cl or F and m is 1, 2 or 3;

R31, 32 independently from each other are $C_1$-$C_6$ alkyl;

R5, R6 Independently from each other are H, $C_1$-$C_{14}$ alkyl, $C_2$-$C_{14}$ alkenyl, aryl, $C_1$-$C_4$ alkylaryl, heteroaryl, $C_1$-$C_4$ alkylheteroaryl, cycloalkyl, $C_1$-$C_4$ alkylcycloalkyl, heterocycloalkyl, $C_4$ alkylheterocycloalkyl, $C_mH_{2m+o-p}Y_p$, or R5 and R6, together with $X_1$—C—C—$X_2$, form a ring with 5, 6, or 7 members, wherein, m is 1 to 6, o is 1, p is 1 to 2m+o;

m is 2 to 6, o is −1, p is 1 to 2m+o; or m is 4 to 6, o is −2, p is 1 to 2m+o; and Y independently from each other is selected from the group consisting of halogen, OH, OR21, $NH_2$, NHR21, NR21R22, SH and SR21;

R4, R7, R8 independently from each other are H, $C_1$-$C_6$ alkyl, CO—R41;

R41 independently from R21 is R21;

X1 is O, S, NH, N—$C_1$-$C_8$ alkyl, or N-cycloalkyl;

X2 is O, S, NH, N—$C_1$-$C_8$ alkyl, or N-cycloalkyl;

Y1 is O, or N—R9, wherein R9, independently from R5, is R5;

Y2 is O, or N—R10, wherein R10, independently from R5, is R5; and, if Y1 or Y2 are N—R9 or N—R10, X2—R6 may be H;

Y3 is O, S, or NH;

or a stereoisomer, tautomer or physiologically tolerable salt thereof.

2. The compound according to claim 1, wherein Formula Ia or Ib adopt the stereochemistry of Formula IIa or IIb 3. The compound according to claim 1, wherein R1 is H, $C_1$-$C_5$ alkyl, or cycloalkyl;

R2 is $C_1$-$C_5$ alkyl, $C_1$-$C_4$ alkylaryl, $C_2$-$C_5$ alkenyl, heteroaryl, $C_1$-$C_4$ alkylheteroaryl, $CHF_2$, $CF_3$, polyol side chain, CHOH—CHOH—CHOH—CHOH—$CH_3$, CHOH—CHOH—CH=CH—$CH_3$, CH=CH—CHOH—CHOH—$CH_3$, $CH_2Y$, $CH_2NH_2$, $CH_2NR21R22$, $CH_2NHCOR23$, $CH_2NHCSR23$, $CH_2SH$, $CH_2S(O)nR21$, $CH_2SCOR21$, $CH_2OH$, $CH_2OR21$, $CH_2OSO_2$—R21, CHO, $CH(OR21)_2$, $CH(SR21)_2$, CN, CH=NOH, CH=NOR21, CH=NOCOR21, CH=N—NHCO—R23, CH=CR24, R25 (trans or cis), COOH, COOR21, CONR21R22, —CH=NR21, —CH=N—NR21R22, —CH=N—$NHSO_2$ aryl, —CH=N—$NHSO_2$ heteroaryl, or CHN—NHCO—R23, wherein Y is F, Cl, Br or I; and wherein X' is NR215, O, or S; and R211, R212, R213, R214, and R215 are independently from each other H or $C_1$-$C_6$ alkyl;

R21, R22 independently from each other are $C_1$-$C_6$ alkyl, cycloalkyl, aryl, $C_1$-$C_4$ alkylaryl, heteroaryl, or $C_1$-$C_4$ alkylheteroaryl;

R23 independently of R21, is R21, a $CH_2$-pyridinium salt, or a $CH_2$-tri-$C_1$-$C_6$ alkylammonium, salt;

R24 independently of R21, is R21, or H, CN, $COCH_3$, COOH, COOR21, CONR21R22, $NH_2$, or NHCOR21;

R25 independently of R21, is R21, or H, CN, $COCH_3$, COOH, COOR21, CONR21R22, $NH_2$, or NHCOR2; or R24, R25 together are $C_4$-$C_8$ cycloalkyl;

R3 is F, Cl, Br, I, $NO_2$, $NH_2$, or NHCOR31;

R31 independently from each other is $C_1$-$C_6$ alkyl;

R5, R6 independently from each other are H, $C_1$-$C_{14}$ alkyl, $C_2$-$C_{14}$ alkenyl, aryl, $C_1$-$C_4$ alkylaryl, heteroaryl, $C_1$-$C_4$ alkyiheteroaryl, cycloalkyl, $C_1$-$C_4$ alkylcycloalkyl, heterocycloalkyl, $C_1$-$C_4$ alkylheterocycloalkyl, $C_mH_{2m+o-p}Y_p$, or R5 and R6, together with $X_1$—C—C—$X_2$, form a ring with 5, 6, or 7 members, wherein, m is 1 to 6, o is 1, p is 1 to 2m+o;
m is 2 to 6, o is −1, p is 1 to 2m+o; or
m is 4 to 6, o is −2, p is 1 to 2m+o; and
Y independently from each other is selected from the group consisting of halogen, OH, OR21, $NH_2$, NHR21, NR21R22, SH and SR21;
R4, R7, R8 independently from each other are H, $C_1$-$C_6$ alkyl, or CO—R41;
R41 independently from R21, is R21;
Y3 is O or S;
or a stereoisomer, tautomer or physiologically tolerable salt thereof.

4. The compounds according to claim 1 in the form of their inclusion compounds with cyclodextrin.

5. The compound according to claim 2 wherein
R1 is H, $C_1$-$C_5$ alkyl, or cycloalkyl;
R2 is $C_1$-$C_5$ alkyl, $C_1$-$C_4$ alkylaryl, $C_2$-$C_5$ alkenyl, heteroaryl, $C_1$-$C_4$ alkylheteroaryl, $CHF_2$, $CF_3$, polyol side chain, CHOH—CHOH—CHOH—CHOH—$CH_3$, CHOH—CHOH—CH=CH—$CH_3$, CH=CH—CHOH—CHOH—$CH_3$, $CH_2Y$, $CH_2NH_2$, $CH_2NR21R22$, $CH_2NHCOR23$, $CH_2NHCSR23$, $CH_2SH$, $CH_2S(O)nR21$, $CH_2SCOR21$, $CH_2OH$, $CH_2OR21$, $CH_2OSO_2$—R21, CHO, $CH(OR21)_2$, $CH(SR21)_2$, CN, CH=NOH, CH=NOR21, CH=NOCOR21, CH=N—NHCO—R23, CH=CR24, R25 (trans or cis), COOH, COOR21, CONR21R22, —CH=NR21, —CH=N—NR21R22,

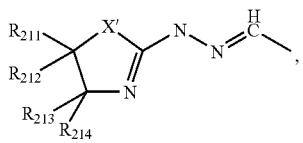

—CH=N—$NHSO_2$ aryl, —CH=N—$NHSO_2$ heteroaryl, CH=N—NHCO—R23,
wherein Y is F, Cl, Br or I;
n is 0, 1 or 2; and
wherein X' is NR215, O, or S; and R211, R212, R213, R214, and R215 are independently from
each other H or $C_1$-$C_6$ alkyl;
R21, R22 independently from each other are $C_1$-$C_6$ alkyl, cycloalkyl, aryl, $C_1$-$C_4$ alkylaryl, heteroaryl, or $C_1$-$C_4$ alkylheteroaryl;
R23 independently of R21, is R21, a $CH_2$-pyridinium salt, or a $CH_2$-tri-$C_1$-$C_6$ alkylammonium salt;
R24 independently of R21, is R21, H, CN, $COOH_3$, COOH, COOR21, CONR21R22, $NH_2$, or NHCOR21;
R25 independently of R21, is R21, H, CN, $COCH_3$, COOH, COOR21, CONR21R22, $NH_2$, or NHCOR21; or
R24, R25 together are $C_4$-$C_8$ cycloalkyl;
R3 is F, Cl, Br, I, $NO_2$, $NH_2$, or NHCOR31;
R31 independently from each other is $C_1$-$C_6$ alkyl;
R5, R6 independently from each other are H, $C_1$-$C_{14}$ alkyl, $C_2$-$C_{14}$ alkenyl, aryl, $C_1$-$C_4$ alkylaryl, heteroaryl, $C_1$-$C_4$ alkylheteroaryl, cycloalkyl, $C_1$-$C_4$ alkylcycloalkyl, heterocycloalkyl, $C_1$-$C_4$ alkylheterocycloalkyl, $C_mH_{2m+o-p}Y_p$ or R5 and R6, together with $X_1$—C—C—$X_2$, form a ring with 5, 6, or 7 members,
wherein, m is 1 to 6, o is 1, p is 1 to 2m+o;
m is 2 to 6, o is −1, p is 1 to 2m+o; or
m is 4 to 6, o is −2, p is 1 to 2m+o; and
Y independently from each other is selected from the group consisting of halogen, OH, OR21, $NH_2$, NHR21, NHR21, NR22, SH and SR21;
R4, R7, R8 independently from each other are H, $C_1$-$C_6$ alkyl, or CO—R41;
R41 independently from R21 is R21;
Y3 is O or S;
or a stereoisomer, tautomer or physiologically tolerable salt thereof.

6. A method of treating a tumor comprising the step of administering to a patient having a tumor selected from the group consisting of lung, renal, prostate, uterine, melanoma and breast tumors an amount of a compound of claim 1 effective to treat said tumor.

7. The method of claim 6 wherein said tumor is a lung tumor.

8. The method of claim 6 wherein said tumor is a renal tumor.

9. The method of claim 6 wherein said tumor is a prostate tumor.

10. The method of claim 6 wherein said tumor is a uterine tumor.

11. The method of claim 6 wherein said tumor is a melanoma.

12. The method of claim 6 wherein said tumor is a breast tumor.

13. A pharmaceutical composition comprising a compound of claim 1 and a pharmaceutically acceptable carrier or adjuvant.

14. A method of treating a tumor comprising the step of administering to a patient having a tumor selected from the group consisting of lung, renal, prostate, uterine, melanoma and breast tumors an amount of a compound of claim 2 effective to treat said tumor.

15. The method of claim 14 wherein said tumor is a lung tumor.

16. The method of claim 14 wherein said tumor is a renal tumor.

17. The method of claim 14 wherein said tumor is a prostate tumor.

18. The method of claim 14 wherein said tumor is a uterine tumor.

19. The method of claim 14 wherein said tumor is a melanoma.

20. The method of claim 14 wherein said tumor is a breast tumor.

21. A pharmaceutical composition comprising a compound of claim 2 and a pharmaceutically acceptable carrier or adjuvant.

* * * * *

UNITED STATES PATENT AND TRADEMARK OFFICE
CERTIFICATE OF CORRECTION

PATENT NO. : 7,244,741 B2 Page 1 of 1
APPLICATION NO. : 10/520421
DATED : July 17, 2007
INVENTOR(S) : Werner Simon et al.

It is certified that error appears in the above-identified patent and that said Letters Patent is hereby corrected as shown below:

In the Claims:

In Claim 1, in the definition of R5 and R6, at column 19, line 22, "$C_4$ alkylheterocycloalkyl," should read -- $C_1$-$C_4$ alkylheterocycloalkyl --; and In Claim 3, in the definition of R25 at column 20, line 56, "NHCOR2" should read -- NHCOR21 --.

In Claim 5, in the definition of Y, at column 22, line 10, "NHR21, NR22" should read -- NR21R22" --.

Signed and Sealed this

Eighth Day of July, 2008

JON W. DUDAS
*Director of the United States Patent and Trademark Office*